United States Patent [19]
Yamaguchi et al.

[11] Patent Number: 5,371,296
[45] Date of Patent: Dec. 6, 1994

[54] 4,4-DIMETHYL-1-PHENYLPENTANE-1,3-DIONE DERIVATIVE AND UV RAY ABSORBENT AND COSMETIC CONTAINING THE SAME

[75] Inventors: Masakazu Yamaguchi; Akira Kawamata; Genji Imokawa; Kouichi Niinaka, all of Tochigi, Japan

[73] Assignee: KAO Corporation, Tokyo, Japan

[21] Appl. No.: 853,078

[22] Filed: Mar. 17, 1992

[30] Foreign Application Priority Data

Mar. 18, 1991 [JP] Japan .................. 3-052700
Mar. 19, 1991 [JP] Japan .................. 3-054932

[51] Int. Cl.$^5$ .................. C07C 49/82; A61K 7/34; A61K 7/42
[52] U.S. Cl. .................. 568/335; 424/59; 424/66
[58] Field of Search .............. 424/59; 568/335; 556/1

[56] References Cited

U.S. PATENT DOCUMENTS

| | | | |
|---|---|---|---|
| 2,530,273 | 11/1950 | Hook et al. | 568/335 X |
| 3,937,737 | 2/1976 | Eiglmeier | 568/335 |
| 4,065,502 | 12/1977 | MacKay et al. | 568/335 |
| 5,191,121 | 3/1993 | Yamada et al. | 564/305 |

FOREIGN PATENT DOCUMENTS

| | | | |
|---|---|---|---|
| 376511 | 7/1990 | European Pat. Off. | 424/59 |
| 0416564 | 3/1991 | European Pat. Off. | 424/59 |

OTHER PUBLICATIONS

Chem. Abs., 1989, vol. 111 (18):163961p, Yoshioka.
Chem. Abs., 1986, vol. 105(9):78293d, Yoshioka (I).
European Search Report, Sep. 28, 1992, EP 92 10 4695.
Chemical Abstracts, vol. 69, 1968, Columbus, Ohio, US; Abstract No. 10157V, Shalygin, A. F.: "Synthesis of some aromatic amino diketones", p. 959, col. 1.

*Primary Examiner*—Dale R. Ore
*Attorney, Agent, or Firm*—Sughrue, Mion, Zinn, Macpeak & Seas

[57] ABSTRACT

A 4,4-Dimethyl-1-phenylpentane-1,3-dione derivatives represented by the following formula (1):

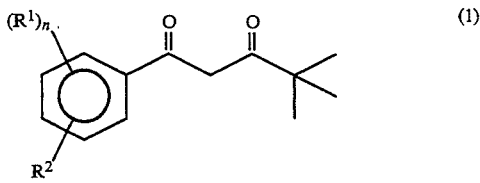

wherein all symbols are defined in the disclosure, is disclosed. An ultraviolet ray absorbent and a cosmetic comprising the derivative are also disclosed. The derivative of the present invention have excellent ultraviolet ray absorbing performance and superior light stability, and the ultraviolet ray absorbent and cosmetic comprising the derivative have excellent effect to prevent sunburn.

2 Claims, No Drawings

4,4-DIMETHYL-1-PHENYLPENTANE-1,3-DIONE DERIVATIVE AND UV RAY ABSORBENT AND COSMETIC CONTAINING THE SAME

FIELD OF THE INVENTION

This invention relates to a novel 4,4-dimethyl-1-phenylpentane-1,3-dione derivative having excellent ultraviolet ray absorbing performance and superior light stability, as well as to an ultraviolet ray absorbent and a cosmetic each comprising the derivative and having excellent sunburn preventing effect.

BACKGROUND OF THE INVENTION

It is known that ultraviolet rays cause various changes in the skin. In the field of skin science, ultraviolet rays are divided into long wavelength ultraviolet ray (400–320 nm), medium wavelength ultraviolet ray (320–290 nm) and short wavelength ultraviolet ray (290 nm or shorter), which are called UV-A, UV-B and UV-C, respectively. Ultraviolet rays in the sunlight consist of UV-A and UV-B, since UV-C hardly reaches the earth due to absorption in the ozone layers.

When the skin is irradiated with a certain quantity of UV-B, various changes occur in the skin such as formation of erythema or bulla and acceleration of melanism which subsequently causes pigmentation. Destruction of the ozone layers in the sky caused by the recently increasing air pollution led to a grave social problem, because such a destruction increases quantity of UV-B in the sunlight. On the other hand, irradiation with UV-A not only leads to immediate onset of melanism in the skin (immediate melanism) but also changes conditions of elastic fibers in blood vessel walls and connective tissues because its energy penetrates epidermis and reaches dermal side of the skin. It is considered in general that such functions of both UV-A and UV-B accelerate aging of the skin, cause generation of spots, wrinkles, freckles and the like and, in a long-term manner, cause skin carcinoma.

With revelation of the influence of ultraviolet rays on the human skin, attempts have been made to develop a compound which can absorb UV-A and UV-B. It is desirable that such an ultraviolet ray absorbent can satisfy all necessary requirements which include: (1) complete absorption of UV-A or UV-B light as far as is possible; (2) stable to light and heat; (3) no toxicity or stimulus to the skin or other hazardous effects; (4) prolonged action; and (5) excellent compatibility with a cosmetic base.

Dibenzoylmethane derivatives have been used as UV-A absorbents, and derivatives of cinnamic acid esters, benzophenone, p-aminobenzoic acid, salicylic acid and the like have been used as UV-B absorbents.

These prior art ultraviolet ray absorbents, however, do not fully satisfy the aforementioned requirements. Especially, they have inferior stability to light and therefore are decomposed or become reactive when exposed to ultraviolet rays as described in *Int. J. Cosmetic Science*, Vol.10, p.53 (1988). Such a decomposition spoils prolonged action of the prior art ultraviolet ray absorbents and also the decomposed products themselves or their reaction products with compounding ingredients exert significant influence on the skin as described in *Fragrance Journal*, Vol.84, p.34 (1987).

In consequence, great concern has been directed toward the development of an ultraviolet ray absorbent which can satisfy all of the aforementioned requirements, especially excellent stability to light.

SUMMARY OF THE INVENTION

Taking such circumstances into consideration, the inventors of the present invention have conducted intensive studies and found that a 4,4-dimethyl-1-phenylpentane-1,3-dione derivative represented by formula (1) which is described in the following can protect the skin from ultraviolet ray absorption due to their excellent ultraviolet ray absorbing performance and that the derivative is markedly stable to light and have excellent solubility in oil. The present invention has been accomplished on the basis of these findings.

Accordingly, the present invention provides a 4,4-dimethyl-1-phenylpentane-1,3-dione derivative represented by the following formula (1):

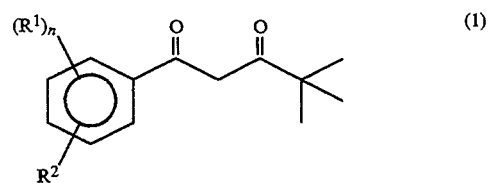

wherein $R^1$, which may be the same or different from each other, each represents an alkoxy group, an alkenyloxy group, an alkyl group having 1 to 8 carbon atoms, an aryl group having 6 to 10 carbon atoms, an acyl group having 2 to 10 carbon atoms and hydroxyl group, and two $R^1$'s may combine to form a methylenedioxy group;

n is an integer of 0 to 3; and $R^2$ represents a dialkylamino group, an alkoxy group or a group represented by the following formula:

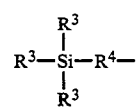

wherein $R^3$, which may be the same or different from each other, each presents an alkyl group having 1 to 6 carbon atoms and a phenyl group; and $R^4$ is an alkylene group having 2 to 3 carbon atoms or an alkyleneoxy group having 2 to 11 carbon atoms;

provided that, when $R^2$ is a dialkylamino group, n is 0 or 1, and $R^1$ is an alkoxy group or an alkenyloxy group; and further provided that, when $R^2$ is an alkoxy group, n is 1 and $R^1$ is not the same alkoxy group as $R^2$.

The present invention also provides an ultraviolet ray absorbent and a cosmetic each comprising the above derivative.

Other objects and advantages will be made apparent as the description progresses.

DETAILED DESCRIPTION OF THE INVENTION

In formula (1) in accordance with the present invention, examples of the alkoxy group represented by $R^1$ or $R^2$ include alkoxy groups having 1 to 8 carbon atoms such as methoxy, ethoxy, n-propoxy, iso-propoxy, butoxy, t-butoxy, pentyloxy, hexyloxy, heptyloxy, octyloxy and the like groups. As to other groups represented by $R^1$, specific examples of the alkyl group having 1 to 8 carbon atom include methyl, ethyl, n-propyl, iso-propyl, n-butyl, t-butyl, pentyl, hexyl, heptyl, octyl and the like groups; specific examples of the aryl group having 6 to 10 carbon atoms include phenyl, tolyl, xylyl, naphthyl and the like groups; specific examples of the acyl group having 2 to 10 carbon atoms include acetyl, propionyl, butanoyl, benzoyl and the like groups; and examples of the alkenyloxy group include those having 2 to 8 carbon atoms such as allyloxy, butenyloxy, pentenyloxy, hexenyloxy and the like groups. Further, two $R^1$'s may combine together to form a methylenedioxy group. Among these groups, a lower alkoxy group having 1 to 4 carbon atoms is preferred as $R^1$.

Examples of the dialkylamino group represented by $R^2$ include those which have two alkyl groups of 1 to 8 carbon atoms, such as dimethylamino, diethylamino, dipropylamino, dibutylamino, diisopropylamino and the like groups. Among these groups, dimethylamino group and diethylamino group are preferred as $R^2$.

Specific examples of the alkyl group having 1 to 6 carbon atoms represented by $R^3$ include methyl, ethyl, propyl, butyl, pentyl, hexyl and the like groups, of which a lower alkyl group having 1 to 5 carbon atoms is particularly preferred.

Specific examples of the alkylene group having 2 to 3 carbon atoms represented by $R^4$ include ethylene, propylene and the like groups; and specific examples of the alkyleneoxy group having 2 to 11 carbon atoms include ethyleneoxy, propyleneoxy, undecyleneoxy and the like groups, of which propyleneoxy group is particularly preferred.

In formula (1), when $R^2$ is a dialkylamino group, n is 0 or 1, and $R^1$ is an alkoxy group or an alkenyloxy group; and when $R^2$ is an alkoxy group, n is 1 and $R^1$ is not the same alkoxy group as $R^2$.

As the position of $R^1$ and $R^2$ on the phenyl ring of the 4,4-dimethyl-1-phenylpentane-1,3-dione derivative of formula (I) of the present invention, the 3, 4 and 5-position in relation to the pentane group are preferred.

The 4,4-dimethyl-1-phenylpentane-1,3-dione derivative (1) of the present invention can be produced, for example, by either of the following methods (a) and (b) in accordance with usually used means as disclosed, for example, in *J. Am. Chem. Soc.*, Vol.80, p.4891 (1958); *J. Chromatogr.*, Vol.312, p.109 (1984); and *J. Polym. Sci. Polym. Chem. Ed.*, Vol.20, p. 3079 ( 1982 ).

Method (a):

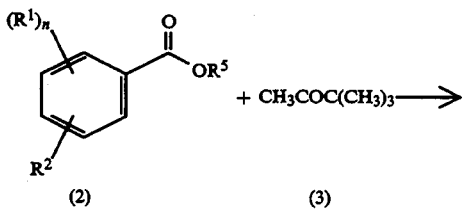

(2)      (3)

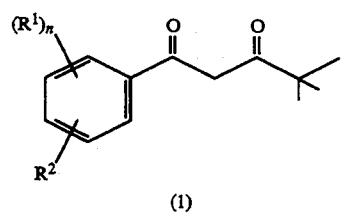

(1)

wherein $R^1$ represents a methyl group, an ethyl group or an n-propyl group or an n-butyl group; and $R^1$, $R^2$ and n are as defined above.

In the above reaction system, the 4,4-dimethyl-1-phenylpentane-1,3-dione derivative (1) is obtained by condensation reaction of a benzoate compound (2) with pinacolone (3). Preferably, the reaction of method (a) may be carried out in a solvent such as anhydrous tetrahydrofuran, toluene, xylene or the like in the presence of a base as a catalyst at a temperature of from 20° to 150° C. for a duration of from some tens of minutes to 10 hours. Examples of the base to be used include for instance: metal hydrides such as sodium hydride; alkylated metals such as butyllithium; amines such as triethylamine; metal amides such as sodium amide; and metal alkoxides such as sodium methoxide.

Method (b):

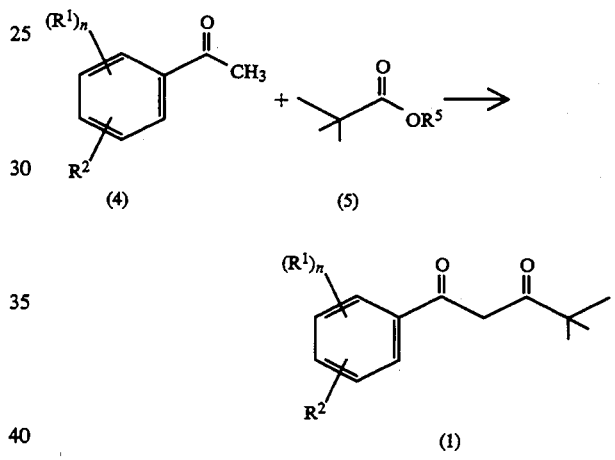

(4)      (5)

(1)

wherein $R^1$, $R^2$, $R^5$ and n are as defined above.

In the above reaction system, the 4,4-dimethyl-1-phenylpentane-1,3-dione derivative (1) is obtained by condensation reaction of an acetylbenzene derivative (4) with an ester compound (5). The ester compound (5) to be used in the reaction may be selected from methyl pivalate, ethyl pivalate, propyl pivalate, butyl pivalate and the like. The reaction of method (b) may be effected under similar conditions to those of the method (a).

On the other hand, a 4,4-dimethyl-1-phenylpentane-1,3-dione derivative (1) of the present invention in which $R^2$ is a group represented by the following formula:

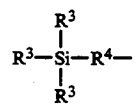

may be produced, for instance, in accordance with the following method (c).

Method ( c ):

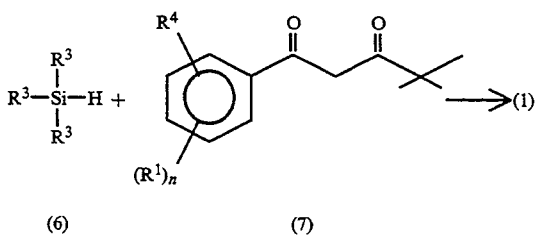

wherein R[6] represents an ω-alkenyl group having 2 to 3 carbon atoms or an ω-alkenyloxy group having 2 to 11 carbon atoms; and R[1], R[3], R[4] and n are as defined above.

In this reaction system, the 4,4-dimethyl-1-phenylpentane-1,3-dione derivative of the present invention is obtained by hydrosilylation reaction of a silane derivative (6) with a benzoylpinacolone derivative (7).

The silane derivative (6) to be used as a starting material can be obtained easily as a commercial article, and the benzoylpinacolone (7) can be produced, for example, by either of the aforementioned methods (a) and (b) in accordance with usually used means as disclosed, for example, in J. Am. Chem. Soc., Vol.80, p.4891 (1958); J. Chromatogr., Vol.312, p.109 (1984); and J. Polym. Sci. Polym. Chem. Ed., Vol.20, p.3079 (1982).

The reaction of the silane derivative (6) with the benzoylpinacolone derivative (7) is carried out in the presence of a catalyst which is selected from usually used catalysts in hydrosilylation reaction including: free radical initiators; photoinitiators; metal complex compounds such as of ruthenium, rhodium, palladium, osmium, iridium, platinum and the like; and their supported forms on silica gel or alumina. Of these catalysts, chloroplatinic acid, Speier reagent (an isopropyl alcohol solution of chloroplatinic acid) and the like are particularly preferable. Although not strictly limited, the catalyst may be used in an amount of from $10^{-6}$ to $10^{-1}$ mole per 1 mole of the benzoylpinacolone derivative to be used.

Though not essential, the reaction in method (c) may be effected in an appropriate solvent if necessary. Types of the reaction solvents are not strictly limited, provided that they do not inhibit the reaction. Examples of the reaction solvents include: hydrocarbon solvents such as pentane, hexane, cyclohexane and the like; benzene solvents such as benzene, toluene, xylene and the like; ether solvents such as diethyl ether, diisopropyl ether, tetrahydrofuran and the like; and alcohol solvents such as methanol, ethanol, isopropyl alcohol, butanol and the like. When an alcohol solvent is used, it is preferable to use a pH-controlling agent such as potassium acetate in order to prevent or inhibit dehydrogenation between Si—H and —OH as disclosed, for example, in JP-A-57-149290 (the term "JP-A" as used herein means an "unexamined published Japanese Patent Application").

Though the reaction progresses at 0° to 200° C., it may preferably be carried out at a temperature of from 0° to 100° C. in method (c) taking reaction rate, coloring of the product and the like into consideration. Preferably, the reaction may be carried out for a period of from 0.5 to 24 hours.

As the ultraviolet ray absorbent of the present invention, at least one of the 4,4-dimethyl-1-phenylpentane-1,3-dione derivative (1) may be used as it is, but preferably as its mixture with a carrier. Any type of carriers may be used in the form of solid, liquid, emulsion, foam, gel and the like, provided that they are inert to the 4,4-dimethyl-1-phenylpentane-1,3-dione derivative (1). Specific examples of such carriers include water, alcohols, fats and oils (for instance, a hydrocarbon oil, a fatty acid ester, a long chain alcohol, silicone oil and the like), fine particles (starch, talc and the like for instance) and a low boiling point hydrocarbon or a halogenated hydrocarbon which is used as an aerosol injection agent.

In addition, the ultraviolet ray absorbent of the present invention may be mixed with other components such as an antiseptic agent, a perfume, a coloring agent, a surface active agent and the like, provided-that these additives do not spoil ultraviolet ray absorbing function of the 4,4-dimethyl-1-phenylpentane-1,3-dione derivative (1).

The cosmetic of the present invention is characterized in that it comprises the 4,4-dimethyl-1-phenylpentane-1,3-dione derivative (1) and is produced in the usual way by mixing a usually employed cosmetic base material with at least one of the 4,4-dimethyl-1-phenylpentane-1,3-dione derivative (1), by selecting a suitable type which has affinity for the base material. The inventive cosmetic can be made into various forms such as creams, solutions, oils, sprays, sticks, emulsions, foundations, ointments and the like. In other words, by selecting a matched type of the 4,4-dimethyl-1-phenylpentane-1,3-dione derivative (1) with a cosmetic base material to be used, the cosmetic material of the present invention can be made into various cosmetic forms having ultraviolet ray absorbing function, including skin care cosmetics such as oil-based cosmetic oils, oily creams and emulsions in which a large quantity of oil is used, weakly oily creams and emulsions in which a large quantity of water is used, water-based lotions and the like, as well as makeup cosmetics such as oil-based foundations, lipsticks and the like.

Examples of suitable base materials and solvents include: hydrocarbons such as solid or liquid paraffin, crystal oil, ceresin, ozokerite, montan wax and the like; vegetable or animal fats and oils and waxes such as olive oil, earth wax, carnauba wax, lanolin, spermaceti wax and the like; fatty acids and esters thereof such as stearic acid, palmitic acid, oleic acid, glycerine monostearate, glycerine distearate, glycerine monooleate, isopropyl myristate, isopropyl stearate, butyl stearate and the like; and alcohols such as ethyl alcohol, isopropyl alcohol, cetyl alcohol, stearyl alcohol, palmityl alcohol, hexyldodecyl alcohol and the like. Also useful are polyhydric alcohols having moisture-keeping function such as glycol, glycerol, sorbitol and the like.

In the ultraviolet ray absorbent and cosmetic of the present invention, the 4,4-dimethyl-1-phenylpentane-1,3-dione derivative (1) may be blended in an amount of from 0.1 to 20% by weight, preferably from 0.5 to 10% by weight, based on the weight of the whole components, though not strictly limited since the amount may vary depending on the product forms.

It is preferable to use the ultraviolet ray absorbent and cosmetic of the present invention as common sunburn preventing cosmetics by combining the 4,4-dimethyl-1-phenylpentane-1,3-dione derivatives (1) with other UV-B or UV-A absorbents. Examples of such UV-B absorbents include p-methylbenzylidene-D(L)-camphor or its sodium sulfonate salt, 2-phenylbenzimidazole-5-sulfonic acid sodium salt, 3,4-dimethylphenyl glyoxylic acid sodium salt, 4-phenylbenzophenone, 4-phenylbenzophenone-2'-carboxylic acid isooctyl ester, p-methoxycinnamic acid ester, 2-phenyl-5-methylbenzoxazole, p-dimethylaminobenzoic acid esters and the like. Examples of UV-A absorbents include 4-methoxy-2'-carboxydibenzoylmethane, 4-methoxy-4'-t-butyldibenzoylmethane, 4-isopropyldibenzoylmethane, 2-hydroxy-4-methoxybenzophenone, dibenzylidene camphors and the like.

In addition to the aforementioned components, the cosmetic of the present invention may further contain various additive agents in such amounts that they do not spoil the effects of the present invention. Examples of such additive agents include: generally employed W/O type and O/W type emulsifying agents; thickeners such as methyl cellulose, ethyl cellulose, carboxymethyl cellulose, polyacrylic acid, tragacanth, agar, gelatin and the like; and perfumes, antiseptic agents, moisture-keeping agents, emulsification stabilizers, active drug ingredients, physiologically acceptable coloring agents and the like.

The following examples are provided to further illustrate the present invention. Unless otherwise indicated, all percents are by weight.

EXAMPLE 1

Synthesis of 1-(3-dimethylaminophenyl)-4,4-dimethylpentane-1,3-dione (a compound of formula (1) in which $R^2$ is 3-$(CH_3)_2N$ and is 0. (Compound (1a).):

A 100 ml three-necked flask equipped with a stirrer, a dropping funnel, a reflux condenser and a nitrogen-introducing tube was charged with 2.08 g (31 mmol) of a 60% sodium hydride and 5.0 g (26 mmol) of ethyl 3-dimethylaminobenzoate, and these compounds were mixed and dispersed in 40 ml of tetrahydrofuran. After reflux by heating, 3.0 g (30 mmol) of pinacolone was added dropwise carefully to the thus prepared mixture, followed by 3 hours of heating with agitation. After spontaneous cooling, the resulting reaction mixture was poured in 50 ml of a 1N hydrochloric acid and organic materials were extracted twice with chloroform. Thus extracted materials were washed thoroughly with water and then dried over anhydrous magnesium sulfate. A yellow oily material was obtained by solvent removal. Thereafter, the thus obtained yellow oily material was subjected to Kugelrohr distillation at 200° C. under 1 mmHg and the resulting sample was crystallized from hexane to obtain 4.81 g (75% in yield) of the compound of interest as a yellow solid substance. This compound is hereinafter referred to as Compound (1a).

$^1$H-NMR (CCl$_4$,δ): 1.39 (9H, s, t-Bu), 2.99 (6H, s, N—CH$_3$), 6.31 (1H, s), 6.90 (1H, dd, J=3 Hz, 12 Hz, Aromatic), 7.25-7.41 (3H, m, Aromatic), 16.26 (1H, bs)

EXAMPLE 2

Synthesis of 1-(4-dimethylaminophenyl)-4,4-dimethylpentane-1,3-dione (a compound of formula (1) in which $R^2$ is 4-$(CH_3)_2N$ and n is 0. (Compound (1b)):

A 100 ml three-necked flask equipped with a stirrer, a dropping funnel, a reflux condenser and a nitrogen-introducing tube was charged with 2.08 g (31 mmol) of a 60% sodium hydride and 5.0 g (26 mmol) of ethyl 4-dimethylaminobenzoate, and these compounds were mixed and dispersed in 40 ml of tetrahydrofuran. After reflux by heating, 3.0 g (30 mmol) of pinacolone was added dropwise carefully to the thus prepared mixture, followed by 3 hours of heating with agitation. After spontaneous cooling, the resulting reaction mixture was poured in 50 ml of a 1N hydrochloric acid and organic materials were extracted twice with chloroform. Thus extracted materials were washed thoroughly with water and then dried over anhydrous magnesium sulfate. A yellow oily material was obtained by solvent removal. Thereafter, the thus obtained yellow oily material was subjected to Kugelrohr distillation at 150° C. under 1 mmHg and the resulting sample was crystallized from hexane to obtain 4.50 g (70% in yield) of the compound of interest as a yellow solid substance. This compound is hereinafter referred to as Compound (1b).

Melting point: 61.5°-61.8° C. IR ($\nu$ KBr, cm$^{-1}$): 2960, 2940, 1610, 1570, 1520, 1440, 1380, 1300, 1190, 1130, 1070, 1030, 930, 850, 830, 800, 720, 690, 600

$^1$H-NMR (CCl$_4$,δ): 1.23 (9H, s, t-Bu), 3.03 (6H, s, N—CH$_3$), 6.20 (1H, s), 6.65 (2H, d, J=9 Hz, Aromatic), 7.83 (2H, d, J=9 Hz, Aromatic), 16.87 (1H, bs)

EXAMPLE 3

(1) Synthesis of 1-(4-allyloxy-3-methoxyphenyl)-4,4-dimethylpentane-1,3-dione (a compound of formula (1) in which $R^1$ is 4—$CH_2$=$CHCH_2O$, $R^2$ is 3—$CH_3O$ and n is 1. (Compound (1c)):

(1) Synthesis of 4-allyloxy-3-methoxyacetophenone:

A 1000 ml three-necked flask equipped with a stirrer, a dropping funnel, a reflux condenser and a nitrogen-introducing tube was charged firstly with 300 ml of tetrahydrofuran and then with 150 g (0.90 mol) of acetovanillone and 149.3 g (1.08 mol) of potassium carbonate, and the mixture was subjected to reflux by heating with vigorous stirring. To this was carefully added 131.1 g (1.08 mol) of allyl bromide in dropwise manner, followed by overnight heating and agitation. To the resulting reaction mixture was further added a mixture consisting of 131.1 g (1.08 mol) of allyl bromide and 100 ml of dimethylformamide, followed by 8 hours of reflux by heating. After spontaneous cooling, solid materials were removed from the resulting reaction mixture by filtration, washed thoroughly with 1000 ml of dichloromethane and then added to the filtrate. The resulting organic layer was washed with 50 ml of a 2N hydrochloric acid and 800 ml of water and then dried over anhydrous magnesium sulfate. A brown oily material was obtained by removing anhydrous magnesium sulfate by filtration and subsequently distilling off the solvent. Thereafter, the thus obtained oily material was subjected to silica gel column chromatography using hexane/ethyl acetate (2/1 (v/v)) as a developer to obtain 174.8 g (94% in yield) of 4-allyloxy-3-methoxyacetophenone as a yellow oily substance.

IR ($\nu$ KBr, cm$^{-1}$): 3090, 3000, 2940, 2880, 1740, 1680, 1590, 1510, 1470, 1420, 1360, 1270, 1220, 1180, 1150, 1080, 1020, 1000, 930, 880, 810, 640, 570

(2) Synthesis of 1-(4-allyloxy-3-methoxyphenyl)-4,4-dimethylpentane-1,3-dione:

A 1000 ml three-necked flask equipped with a stirrer, a dropping funnel, a reflux condenser and a nitrogen-introducing tube was charged firstly with 200 ml of tetrahydrofuran and then with 24 g (0.6 mol) of a 60% sodium hydride to be dispersed in the solvent, and the mixture was subjected to reflux by heating. To this was carefully added a 200 ml tetrahydrofuran solution in which 61.9 g (0.3 mol) of 4-allyloxy-3-methoxyacetophenone and 39.1 g (0.30 mol) of ethyl pivalate have been dissolved, in dropwise manner over about 3.5 hours, followed by overnight heating and agitation. After cooling in an ice bath, 300 ml of a 2N hydrochloric acid was added carefully to the reaction mixture which was then washed twice with 100 ml of a saturated sodium chloride solution. The resulting organic layer was dried over anhydrous magnesium sulfate and the solvent was distilled off to obtain a brown oily material. Thereafter, the thus obtained oily material was subjected to silica gel column chromatography using hexane/ethyl acetate (2/1 (v/v)) as a developer to obtain 74.6 g (86% in yield) of the compound of interest, 1-(4-allyloxy-3-methoxyphenyl)-4,4-dimethylpentane-1,3-dione, as a pale red oily substance. This compound is hereinafter referred to as Compound (1c).

Melting point: 40.0° C. IR ($\nu$ KBr, cm$^{-1}$): 3090, 2960, 2930, 2870, 2620, 1710, 1680, 1600, 1520, 1470, 1430, 1370, 1340, 1280, 1210, 1180, 1150, 1140, 1080, 1020, 1000, 930, 880, 730, 640, 620, 570, 480

$^1$H-NMR (CCl$_4$, $\delta$): 1.23 (9H, s, t-Bu), 3.83 (3H, s, O—CH$_3$), 4,43–4.60 (2H, m, O—CH$_2$), 5.06–5.50 (2H, m, Allylic-CH$_2$), 5.70–6.10 (1H, m, Allylic-CH), 6.05 (1H, s), 6.67 (1H, d, J=9 Hz, Aromatic), 7.17–7.32 (2H, m, Aromatic), 16.76 (1H, bs)

EXAMPLE 4

Synthesis of 1-(3-methoxy-4-propoxyphenyl)-4,4-dimethylpentane-1,3-dione (a compound of formula (1) in which $R^1$ is 3-CH$_3$O, $R^2$ is 4-CH$_3$CH$_2$CH$_2$O and n is 1) (Compound (1d)):

A 50 ml eggplant type flask equipped with a magnetic stirrer, a dropping funnel, a reflux condenser and a gas-introducing tube was charged with 250 mg of a 5% palladium/carbon dispersed in 25 ml of ethanol and 5.0 g (24 mmol) of 1-(4-allyloxy-3-methoxyphenyl)-4,4-dimethylpentane-1,3-dione. After completely replacing the atmosphere of the reaction system with hydrogen, stirring was continued for 2 hours at room temperature. A light yellow oily material was obtained by removing the palladium/carbon by filtration and subsequently distilling off the solvent. Thereafter, the thus obtained oily material was subjected to silica gel column chromatography using hexane/ethyl acetate (10/1–5/1 (v/v)) as a developer to obtain 4.0 g (80% in yield) of the compound of interest, 1-(3-methoxy-4-propoxyphenyl)-4,4-dimethylpentane-1,3-dione, as an achromatic solid substance. This compound is hereinafter referred to as Compound (1d).

Melting point: 55.5°–56.7° C. IR ($\nu$ KBr, cm$^{-1}$): 3090, 2970, 2940, 2880, 1600, 1520, 1470, 1390, 1300, 1270, 1220, 1180, 1150, 1140, 1070, 1030, 970, 940, 880, 800, 730

$^1$H-NMR (CDCl$_3$, $\delta$): 1.06 (3H, t, J=3 Hz, CH$_3$), 1.25 (9H, s, t-Bu), 1.81–2.00 (2H, m, CH$_2$), 3.93 (3H, s, O—CH$_3$), 4.04 (2H, t, J=7 Hz, O—CH$_2$), 6.24 (1H, s), 6.86–6.91 (1H, m, Aromatic), 7.45–7.55 (2H, m, Aromatic), 16.76 (1H, bs)

TEST EXAMPLE 1

Ultraviolet Ray Absorbing Effect of Compounds of the Invention:

Ultraviolet ray absorbing effect (absorbance) of the compounds of the present invention was measured in accordance with the following procedure. In this instance, 2-hydroxy-4-methoxybenzophenone (UV-A absorbent) and 2-ethylhexyl-p-methoxy cinnamate (UV-B absorbent) were used as comparative compounds. The results are shown in Table 1.

(Measuring procedure)

Each of the compound of the invention and comparative compounds was dissolved in ethanol (99.5%, special grade chemical) to a concentration of $2.5 \times 10^{-5}$ mol/l, and absorbance of the thus prepared solution was measured in a quartz cell (1 cm×1 cm) using a spectrophotometer (U-3410, manufactured by Hitachi, Ltd.).

TABLE 1

| (Ultraviolet Ray Absorbing Effect) | | | | | | |
|---|---|---|---|---|---|---|
| Wave Length | Compound of the Invention | | | | Comparative Compound | |
| (nm) | (1a) | (1b) | (1c) | (1d) | 1 | 2 |
| 290 | 0.291 | 0.138 | 0.227 | 0.238 | 0.40 | 0.54 |
| 300 | 0.370 | 0.139 | 0.290 | 0.289 | 0.28 | 0.60 |
| 310 | 0.381 | 0.140 | 0.371 | 0.360 | 0.24 | 0.64 |
| 320 | 0.327 | 0.173 | 0.500 | 0.483 | 0.25 | 0.52 |
| 330 | 0.226 | 0.270 | 0.590 | 0.593 | 0.25 | 0.27 |
| 340 | 0.137 | 0.430 | 0.578 | 0.579 | 0.21 | 0.08 |
| 350 | 0.078 | 0.620 | 0.404 | 0.420 | 0.13 | 0.02 |
| 360 | 0.066 | 0.798 | 0.223 | 0.231 | 0.06 | 0.01 |
| 370 | 0.066 | 0.830 | 0.304 | 0.073 | 0.03 | 0 |
| 380 | 0.062 | 0.720 | 0.016 | 0.001 | 0.01 | 0 |
| 390 | 0.057 | 0.502 | 0 | 0 | 0 | 0 |
| 400 | 0.042 | 0.252 | 0 | 0 | 0 | 0 |

Notes:
Comparative compound 1: 2-hydroxy-4-methoxy-benzophenone
Comparative compound 2: 2-ethylhexyl-p-methoxy cinnamate These results indicate that the compounds of the present invention have higher effect to absorb UV-A and UV-B ultraviolet rays and therefore higher effect to prevent sunburn than those of the comparative compound, i.e., 2-hydroxy-4-methoxybenzophenone or 2-ethylhexyl-p-methoxy cinnamate.

TEST EXAMPLE 2

Stability of Compounds of the Invention against Ultraviolet Rays:

(Method)

Each of the compound of the invention and comparative compounds was dissolved in a solvent system consisting of a 99.5% ethanol and distilled water (3/2 (v/v)) to a concentration of 2 mmol/l, and the thus prepared solution was exposed to ultraviolet rays for 14 or 65 hours using a xenon light stability meter which can generate a beam having extremely close wavelength and intensity to those of the sunlight. After removing the solvent from the system by distillation, quantitative analysis was carried out and stability of each compound was calculated based on its residual ratio.

The results are shown in Table 2.

TABLE 2

| (Evaluation of Light Stability) | | |
|---|---|---|
| | Residual ratio (%) | |
| Sample | 14 hr. | 65 hr. |
| Compound (1a) | 95 | 82 |
| Compound (1b) | 93 | 80 |
| Compound (1c) | 99 | 95 |
| Compound (1d) | 99 | 97 |
| Comparative Compound 1 | 73 | 29 |
| Comparative Compound 2 | 42 | 10 |

Note:
Comparative compound 1: 4-methoxy-4'-t-butyl-dibenzoylmethane
Comparative compound 2: 2-ethylhexyl-p-methoxy cinnamate As is evident from the results shown in Table 2, the compounds of the present invention have markedly excellent stability against ultraviolet rays in comparison with that of 4-methoxy-4'-t-butyldibenzoylmethane which is generally used as a UV-A absorbent or 2-ethylhexyl-p-methoxy cinnamate which is generally used as a UV-B absorbent.

EXAMPLE 5

(O/W Type Cream)

An O/W type cream was prepared by blending the following composition in a usual way.

| Composition | Amount (% by weight) |
|---|---|
| 1-(3-dimethylaminophenyl)-4,4-dimethyl-pentane-1,3-dione | 2.0 |
| Stearic Acid | 1.0 |
| Lipophilic Monostearic Acid Glyceride | 2.0 |
| Polyoxyethylenesorbitan Monostearate | 1.0 |
| Cetyl Alcohol | 1.0 |
| Stearyl Alcohol | 1.0 |
| Squalane | 10.0 |
| Liquid Paraffin | 20.0 |
| Vaseline | 5.0 |
| Butylparaben | 0.1 |
| Methylparaben | 0.1 |
| Triethanolamine | 1.0 |
| Glycerol | 10.0 |
| Perfume | Appropriate Amount |
| Water | balance |
| Total | 100.0 |

EXAMPLE 6

(W/O Type Cream)

A W/O type cream was prepared by blending the following composition in a usual way.

| Composition | Amount (% by weight) |
|---|---|
| 1-(4-dimethylaminophenyl)-4,4-dimethyl-pentane-1,3-dione | 2.0 |
| Sorbitan Sesquioleate | 4.0 |
| Aluminum Stearate | 0.5 |
| Cetyl Alcohol | 4.0 |
| Liquid Paraffin | 16.0 |
| Squalane | 10.0 |
| Isopropyl Myristate | 5.0 |
| Sodium Benzoate | 0.3 |
| Glycerol | 10.0 |
| Perfume | Appropriate Amount |
| Water | balance |
| Total | 100.0 |

Example 7

(O/W Type Emulsion)

An O/W type emulsion was prepared by blending the following composition in a usual way.

| Composition | Amount (% by weight) |
|---|---|
| 1-(4-allyloxy-3-methoxyphenyl)-4,4-dimethylpentane-1,3-dione | 3.0 |
| Stearic Acid | 2.0 |
| Sorbitan Monostearate | 1.5 |
| Polyoxyethylenesorbitan Monostearate | 1.0 |
| Cetyl Alcohol | 0.4 |
| Stearyl Alcohol | 0.3 |
| Isopropyl Myristate | 7.0 |
| Squalane | 5.0 |
| Liquid Paraffin | 5.0 |
| Solid Paraffin | 2.0 |
| Ethylparaben | 0.1 |
| Methylparaben | 0.1 |
| Carbopol | 0.2 |
| Potassium Hydroxide | 0.4 |
| Perfume | Appropriate Amount |
| Water | balance |
| Total | 100.0 |

EXAMPLE 8

(Lotion)

A lotion was prepared by blending the following composition in a usual way.

| Composition | Amount (% by weight) |
|---|---|
| 1-(4-allyloxy-3-methoxyphenyl)-4,4-dimethylpentane-1,3-dione | 2.0 |
| Polyoxyethylene(23)lauryl Ether | 4.0 |
| Ethanol | 10.0 |
| Glycerol | 3.0 |
| Dipropylene Glycol | 7.0 |
| Lactic Acid | 0.05 |
| Sodium Lactate | 0.12 |
| Methylparaben | 0.1 |
| Perfume | Appropriate Amount |
| Coloring Matter | Trace |
| Water | Balance |
| Total | 100.0 |

Example 91

Synthesis of 1-(4-(3,3-diethylmethylsilyl)propoxy-3-methoxyphenyl)-4,4-dimethylpentane-1,3-dione (a compound of formula (1) in which $R^1$ is $OCH_3$, $R^2$ is

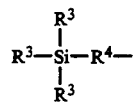

wherein $R^3$ is $CH_3$, $C_2H_5$ and $C_2H_5$, $R^2$ is $CH_2CH_2CH_2O$ and n is 1) (Compound (1e))

(1) Synthesis of 1-(4-allyloxy-3-methoxyphenyl)-4,4-dimethylpentane-1,3-dione:

A 1000 ml three-necked flask equipped with a stirrer, a dropping funnel, a reflux condenser and a nitrogen-introducing tube was charged firstly with 200 ml of tetrahydrofuran and then with 24 g (0.6 mol) of a 60% sodium hydride to be dispersed in the solvent, and the mixture was subjected to reflux by heating. To this was carefully added a 200 ml tetrahydrofuran solution in which 61.9 g (0.3 mol) of 4-allyloxy-3-methoxyacetophenone and 39.1 g (0.3 mol) of ethyl pivalate have been dissolved, in dropwise manner over about 3.5 hours, followed by overnight heating and agitation. After cooling in an ice bath, 300 ml of a 2N hydrochloric acid was added carefully to the reaction mixture which was then washed twice with 100 ml of a saturated sodium chloride solution. The resulting organic layer was dried over anhydrous magnesium sulfate and the solvent was distilled off to obtain a brown oily material. Thereafter, the thus obtained oily material was subjected to silica gel column chromatography using hexane/ethyl acetate (2/1 (v/v)) as a developer to obtain 74.6 g (86% in yield) of the title compound as a light red oily substance.

Melting point: 40.0° C. IR ($\nu$ KBr, cm$^{-1}$): 3090, 2960, 2930, 2870, 2620, 1710, 1680, 1600, 1520, 1470, 1430, 1370, 1340, 1280, 1210, 1180, 1150, 1140, 1080, 1020, 1000, 930, 880, 730, 640, 620, 570, 480

$^1$H-NMR( CCl$_4$, $\delta$): 1.23 (s, 9H, t-Bu), 3.83 (S, 3H, O—CH$_3$), 4,43–4.60 (m, 2H, O—CH$_2$), 5.06–5.50 (m, 2H, Allylic-CH$_2$), 5.70–6.10 (m, 1H, Allylic-CH), 6.05 (s, 1H), 6.67 (d, 1H, J=9.0 Hz, Aromatic), 7.17–7.32 (m, 2H, Aromatic), 16.76 (bs, 1H)

(2) Synthesis of 1-(4-(3,3-diethylmethylsilyl)-propoxy-3-methoxyphenyl)-4,4-dimethylpentane-3-dione:

A 30 ml eggplant type flask equipped with a magnetic stirrer, a dropping funnel, a reflux condenser and a nitrogen-introducing tube was charged with 3.0 g (10 mmol) of 1-(4-allyloxy-3-methoxyphenyl)-4,4-dimethyl-pentane-1,3-dione, 3.2 g .(31 mmol) of diethylmethylsilane, about 0.1 ml of a 10% ethanol solution of potassium acetate and about 0.2 ml of a 2% isopropanol solution of chloroplatinic acid hexahydrate in that order, and the thus prepared mixture was stirred at room temperature for 3 hours. After completion of the reaction, the solvents were distilled off to obtain a pale yellow oily material. Thereafter, the thus obtained oily material was subjected to silica gel column chromatography using hexane/ethyl acetate (20/1 (v/v)) as a developer to obtain 3.37 g (83% in yield) of the title compound of interest as an achromatic oily substance. This compound is hereinafter referred to as Compound (1e).

IR ($\nu$ neat, cm$^{-1}$): 2960, 2880, 1600, 1510, 1470, 1280, 1210, 1180, 1150, 1140, 1040, 880, 790, 750

$^1$H-NMR(CDCl$_3$, $\delta$): −0.04 (s, 3H, Si—CH$_3$), 0.49–0.70 (m, 6H, Si—CH$_2$—), 0.93 (s, 6H, Si—CH$_2$—CH$_3$), 1.24 (s, 9H, t-Bu), 1.80–2.02 (m, 2H, —CH$_2$—), 3.94 (s, 3H, O—CH$_3$), 4.02 (t, 2H, J=7.3 Hz, O—CH$_2$), 6.23 (s,1H), 6.94 (d, 1H, J=8.9 Hz, Aromatic), 7.43–7.60 (m, 2H, Aromatic), 16.72 (bs,1H)

TEST EXAMPLE 3

Ultraviolet Ray Absorbing Effect:

Ultraviolet ray absorbing effect (absorbance) of the compound of the invention obtained in Example 9 (Compound (1e)) was measured in accordance with the following procedure. In this instance, 2-hydroxy-4-methoxybenzophenone (UV-A absorbent) and 2-ethyl-hexyl-p-methoxy cinnamate (UV-B absorbent) were used as comparative compounds 1 and 2, respectively. The results are shown in Table 3.

(Measuring procedure)

Each of the compound of the invention and comparative compounds was dissolved in ethanol (99.5%, special grade chemical) to a concentration of 2.5×10$^{-5}$ mol/1, and absorbance of the thus prepared solution was measured in a quartz cell (1 cm×1 cm) using a spectrophotometer (U-3410, manufactured by Hitachi, Ltd.).

TABLE 3

| | (Ultraviolet Ray Absorbing Effect) | | |
|---|---|---|---|
| Wavelength (nm) | Compound (1e) | Comparative Compound | |
| | | 1 | 2 |
| 290 | 0.236 | 0.400 | 0.540 |
| 300 | 0.292 | 0.280 | 0.600 |
| 310 | 0.380 | 0.240 | 0.640 |
| 320 | 0.511 | 0.250 | 0.520 |
| 330 | 0.607 | 0.250 | 0.270 |
| 340 | 0.613 | 0.210 | 0.080 |
| 350 | 0.452 | 0.130 | 0.020 |

TABLE 3-continued

| | (Ultraviolet Ray Absorbing Effect) | | |
|---|---|---|---|
| Wavelength (nm) | Compound (1e) | Comparative Compound | |
| | | 1 | 2 |
| 360 | 0.243 | 0.060 | 0.010 |
| 370 | 0.080 | 0.030 | 0.000 |
| 380 | 0.012 | 0.010 | 0.000 |
| 390 | 0.002 | 0.000 | 0.000 |
| 400 | 0.000 | 0.000 | 0.000 |

As is evident from the results shown in Table 3, the compound of the present invention has higher effect to absorb UV-A and UV-B ultraviolet rays than the comparative compounds and therefore higher effect to prevent sunburn than those of the comparative compounds.

TEST EXAMPLE 4

Stability Against Ultraviolet Ray:

Stability of the compound of the invention obtained in Example 9 (Compound (1e)) against ultraviolet rays was measured in accordance with the following procedure. In this instance, 4-methoxy-4'-t-butyldibenzoylmethane and 2-ethyl-hexyl-p-methoxy cinnamate were used as comparative compounds 3 and 4, respectively. The results are shown in Table 4.

(Method)

Each of the compound of the invention and comparative compounds was dissolved in a solvent system consisting of a 99.5% ethanol and distilled water (3/2 (v/v)) to a concentration of 2 mmol/1, and the thus prepared solution was exposed to ultraviolet rays for 14 or 65 hours using a xenon light stability meter which can generate a beam having extremely close wavelength and intensity to those of the sunlight. After removing the solvents by distillation, quantitative analysis was carried out and stability of each compound was calculated based on its residual ratio, with the results shown in Table 4.

TABLE 4

| (Evaluation of Light Stability) | | |
|---|---|---|
| | Residual Ratio | |
| Sample | 14 hr. (%) | 65 hr. (%) |
| Compound (1e) | >99 | 99 |
| Comparative Compound 3 | 73 | 29 |
| Comparative Compound 4 | 42 | 10 |

As is evident from the results shown in Table 4, the compound of the present invention has markedly excellent stability against ultraviolet rays in comparison with those of the comparative compounds.

EXAMPLE 10

(W/O Type Cream)

A W/O type cream was prepared by blending the following composition in a usual way.

| Composition | Amount (% by weight) |
|---|---|
| 1-(4-(3,3-diethylmethylsilyl)propoxy-3-methoxyphenyl)-4,4-dimethylpentane-1,3-dione | 2.0 |
| Sorbitan sesquioleate | 4.0 |
| Aluminum Stearate | 0.5 |
| Cetyl Alcohol | 4.0 |

-continued

| Composition | Amount (% by weight) |
| --- | --- |
| Liquid Paraffin | 16.0 |
| Squalane | 10.0 |
| Isopropyl Myristate | 5.0 |
| Sodium Benzoate | 0.3 |
| Glycerol | 10.0 |
| Perfume | Appropriate Amount |
| Water | Balance |
| Total | 100.0 |

EXAMPLE 11

(Lotion)

A lotion was prepared by blending the following composition in a usual way.

| Composition | Amount (% by weight) |
| --- | --- |
| 1-(4-(3,3-diethylmethylsilyl)propoxy-3-methoxyphenyl)-4,4-dimethylpentane-1,3-dione | 2.0 |
| Polyoxyethylene(23)lauryl ether | 4.0 |
| Ethanol | 10.0 |
| Glycerol | 3.0 |
| Dipropylene glycol | 7.0 |
| Lactic acid | 0.05 |
| Sodium Lactate | 0.12 |
| Methylparaben | 0.1 |
| Perfume | Appropriate Amount |
| Coloring Matter | Trace |
| Water | Balance |
| Total | 100.0 |

EXAMPLE 12

(O/W Type Emulsion)

An O/W type emulsion was prepared by blending the following composition in a usual way.

| Composition | Amount (% by weight) |
| --- | --- |
| 1-(4-(3,3-diethylmethylsilyl)propoxy-3-methoxyphenyl)-4,4-dimethylpentane-1,3-dione | 3.0 |
| Stearic Acid | 2.0 |
| Sorbitan Monostearate | 1.5 |
| Polyoxyethylene(23)sorbitan Monostearate | 1.0 |
| Cetyl Alcohol | 0.4 |
| Stearyl Alcohol | 0.3 |
| Isopropyl Myristate | 7.0 |
| Squalane | 5.0 |
| Liquid Paraffin | 5.0 |
| Solid Paraffin | 2.0 |
| Ethylparaben | 0.1 |
| Methylparaben | 0.1 |
| Carboxyvinyl Polymer (Carbopol, manufactured by Goodrich Co.) | 0.2 |
| Potassium Hydroxide | 0.4 |
| Perfume | Appropriate Amount |
| Water | Balance |
| Total | 100.0 |

EXAMPLE 13

(O/W Type Cream)

An O/W type cream was prepared by blending the following composition in a usual way.

| Composition | Amount (% by weight) |
| --- | --- |
| 1-(4-(3,3-diethylmethylsilyl)propoxy-3-methoxyphenyl)-4,4-dimethylpentane-1,3-dione | 2.0 |
| Stearic Acid | 1.0 |
| Lipophilic Monostearic Acid Glyceride | 2.0 |
| Polyoxyethylene(23)sorbitan Monostearate | 1.0 |
| Cetyl Alcohol | 1.0 |
| Stearyl Alcohol | 1.0 |
| Squalane | 10.0 |
| Liquid Paraffin | 20.0 |
| Vaseline | 5.0 |
| Butylparaben | 0.1 |
| Methylparaben | 0.1 |
| Triethanolamine | 1.0 |
| Glycerol | 10.0 |
| Perfume | Appropriate Amount |
| Water | Balance |
| Total | 100.0 |

Thus, it is apparent that there have been provided, in accordance with the present invention, novel 4,4-dimethyl-1-phenylpentane-1,3-dione derivatives having excellent ultraviolet ray absorbing function and superior light stability, as well as ultraviolet ray absorbents and cosmetic materials each of which containing the derivative and having excellent sunburn preventing effect.

While the invention has been described in detail and with reference to specific embodiments thereof, it will be apparent to one skilled in the art that various changes and modifications can be made therein without departing from the spirit and scope thereof.

What is claimed is:

1. A 4,4-dimethyl-1-phenylpentane-1,3-dione derivative represented by the following formula (1):

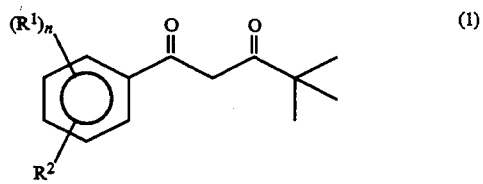

wherein $R^1$, which may be the same or different from each other, each represents an alkoxy group having 1 to 8 carbon atoms, an alkenyloxy group having 2 to 8 carbon atoms, an alkyl group having 1 to 8 carbon atoms, an aryl group having 6 to 10 carbon atoms, an acyl group having 2 to 10 carbon atoms and hydroxyl group, and two $R^1$'s may combine to form a methylenedioxy group;

n is an integer of 0 to 3; and $R^2$ represents a group represented by the following formula:

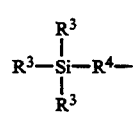

wherein $R^3$, which may be the same or different from each other, each represents an alkyl group having 1 to 6 carbon atoms and a phenyl group;

and $R^4$ is an alkylene group having 2 to 3 carbon atoms or an alkyleneoxy group having 2 to 11 carbon atoms.

2. A derivative of claim 1, wherein said derivative is a compound selected from 1-(3-dimethylaminophenyl)-4,4-dimethylpentane-1,3-dione, 1-(4-dimethylaminophenyl)-4,4-dimethylpentane-1,3-dione, 1-(4-allyloxy-3-methoxyphenyl)-4,4-dimethylpentane-1,3-dione, 1-(3-methoxy-4-propoxyphenyl)-4,4-dimethylpentane-1,3-dione and 1-(4-(3,3-diethylmethylsilyl)propoxy-3-methoxyphenyl)-4,4-dimethylpentane-1,3-dione.

* * * * *